US007604619B2

(12) United States Patent
Eich et al.

(10) Patent No.: US 7,604,619 B2
(45) Date of Patent: Oct. 20, 2009

(54) AMPOULE RECOGNITION

(75) Inventors: Adrian Eich, Wangenried (CH); Stefan Jost, Muehleberg (CH); Rainer Ponzer, Oberburg (CH); Alessandro Sebaste, Basel (CH); Beat Steffen, Saanen (CH); Julian Yeandel, Grosshoechstetten (CH)

(73) Assignee: TecPharma Licensing AG, Burgdorf (CH)

( * ) Notice: Subject to any disclaimer, the term of this patent is extended or adjusted under 35 U.S.C. 154(b) by 27 days.

(21) Appl. No.: 10/809,239

(22) Filed: Mar. 25, 2004

(65) Prior Publication Data

US 2004/0178255 A1 Sep. 16, 2004

Related U.S. Application Data

(63) Continuation of application No. PCT/CH02/00465, filed on Aug. 26, 2002.

(30) Foreign Application Priority Data

Sep. 28, 2001 (DE) ............................... 101 47 973

(51) Int. Cl.
*A61M 5/00* (2006.01)
*G06K 7/00* (2006.01)

(52) U.S. Cl. ....................................... 604/232; 235/439

(58) Field of Classification Search ......... 604/232–234, 604/151–155, 181; 235/439, 454, 462.03, 235/449

See application file for complete search history.

(56) References Cited

U.S. PATENT DOCUMENTS

| | | | | |
|---|---|---|---|---|
| 3,418,456 | A * | 12/1968 | Hamisch et al. | 235/454 |
| 3,585,367 | A * | 6/1971 | Humbarger | 235/454 |
| 5,359,379 | A * | 10/1994 | Kohno et al. | 396/80 |
| 5,681,285 | A | 10/1997 | Ford et al. | |
| 6,019,745 | A * | 2/2000 | Gray | 604/131 |
| 6,042,571 | A | 3/2000 | Hjertman et al. | |
| 6,089,455 | A * | 7/2000 | Yagita | 235/454 |
| 6,110,152 | A | 8/2000 | Kovelman | |
| 6,669,090 | B2 * | 12/2003 | Eilersen | 235/462.03 |
| 2002/0032429 | A1 * | 3/2002 | Hjertman et al. | 604/500 |
| 2003/0006209 | A1 | 1/2003 | Stefen et al. | |

FOREIGN PATENT DOCUMENTS

| | | | |
|---|---|---|---|
| EP | 1 095 668 | A1 | 5/2001 |
| EP | 1095668 | A1 * | 5/2001 |

* cited by examiner

*Primary Examiner*—Kevin C Sirmons
*Assistant Examiner*—Catherine N Witczak
(74) *Attorney, Agent, or Firm*—Dorsey & Whitney LLP; David E. Bruhn

(57) ABSTRACT

An ampoule for use with an administering device such as an injection or infusion apparatus, at least two recognition elements associated with the ampoule, each of which at least two recognition elements can be arranged in one of at least two predetermined positions relative to the ampoule, wherein the at least two predetermined positions are asymmetrically located relative to the ampoule, and an administering device such as an injection or infusion apparatus which can be coupled to the ampoule. In one embodiment, the administering device has at least two associated sensors at predetermined positions in order to recognize the arrangement of the at least two recognition elements associated with an ampoule and, in another embodiment, the administering device has at least one sensor which can be moved relative to an ampoule.

10 Claims, 5 Drawing Sheets

AMPOULE RECOGNITION

CROSS-REFERENCE TO RELATED APPLICATION(S)

This application is a continuation of International Application No. PCT/CH02/00465, filed Aug. 26, 2002, which claims priority to German Application No. 101 47 973.5, filed on Sep. 28, 2001, both of which are incorporated herein in their entirety.

BACKGROUND

The present invention relates to medical devices and treatment methods, including injection or infusion devices, systems, apparatus and methods. More particularly, the present invention relates to an ampoule for use with an administering device such as an injection or infusion apparatus, wherein the ampoule and the administering device have ampoule recognition characteristics or features.

Devices for administering product fluids from ampoules are known in the form of portable injection or infusion apparatus which are used, for example, in insulin treatment. Typically, an ampoule filled with a substance to be administered is coupled to an administering device—often referred to as a pen or an injection pen—in order to administer or dispense the substance contained in the ampoule to a patient via the administering device. There are a multitude of substances which are administered in this way, such as preparations comprising insulin for diabetes, growth hormones (hGH: human Growth Hormone) for disturbed growth, erythropoietin (Epo) for renal insufficiency or general erythrocytopenia, α-interferon for hepatitis or cancer treatment, or potentiating agents to name but a few. The ampoules, which are often geometrically and/or structurally identical, may be filled with various, different substances or with different concentrations of similar substances.

In order to reduce the danger of confusing containers or ampoules containing different substances, it is known to use variously formed or configured administering devices into which only respectively corresponding, complementary or otherwise suitably configured containers or ampoules can be inserted.

A container is known from WO 98/00187, which describes a color coding which can be attached to the container, wherein the coding consists of a number of different colored fields, whereby a property of a container or its contents can be recognized by means of an optical sensor system.

Another container and a device for administering a substance is known from WO 01/56635 A1, belonging to the Applicant, wherein a recognition element is assigned to the container.

SUMMARY

It is an object of the present invention to provide an ampoule and an administering device, wherein various types of ampoules or similar ampoules containing different substances can be automatically recognized and differentiated by the administering device. It is another object of the present invention to minimize incorrect or erroneous recognition and/or use of ampoules.

As used herein, the term "ampoule" refers to any structure or container suitable for accommodating a substance. The container and/or the ampoule can be made of a rigid or stiff material, such as plastic, glass or metal, it can be made of a material which is flexible or elastic, such as a film of plastic, or it can be made from any suitable material or combination of materials. The ampoule can be rotationally symmetrical, cylindrical, parallelepipedal or marsupial and can, in general, exhibit any geometry, as long as a particular and/or variable volume is available. In some embodiments, the volume can range from 0.1 to 1000 ml.

In one embodiment, the present invention comprises an ampoule for use with an administering device such as an injection or infusion apparatus, at least two recognition elements associated with the ampoule, each of which at least two recognition elements can be arranged in one of at least two predetermined positions relative to the ampoule, wherein the at least two predetermined positions are asymmetrically located relative to the ampoule, and an administering device such as an injection or infusion apparatus which can be coupled to the ampoule. In one embodiment, the administering device has at least two associated sensors at predetermined positions in order to recognize the arrangement of the at least two recognition elements associated with an ampoule and, in another embodiment, the administering device has at least one sensor which can be moved relative to an ampoule.

In one embodiment, the present invention comprises an administering device such as an injection or infusion apparatus and an ampoule for use with the administering device, wherein the ampoule comprises at least two associated recognition elements, each of which at least two recognition elements can be arranged in one of at least two predetermined positions relative to the ampoule, wherein the at least two predetermined positions are asymmetrically located relative to the ampoule, and wherein, in one embodiment, the administering device has at least two associated sensors at predetermined positions in order to recognize the arrangement of the at least two recognition elements associated with an ampoule and, in another embodiment, the administering device has at least one sensor which can be moved relative to an ampoule.

In some embodiments, an ampoule in accordance with the present invention is preferably generally cylindrical and suitable for use in an injection or infusion apparatus, and can preferably accommodate a substance to be administered, in particular a medicinal fluid for self-administering. In some embodiments, an ampoule in accordance with the present invention comprises at least two recognition elements, wherein the recognition elements are associated with the ampoule, for example, arranged on it, integral with it, or fixedly connected to it. Each of the at least two recognition elements has a selected predetermined position relative to the ampoule. The position(s) can be infinitely varied, or can comprise at least two or more predetermined positions. In some embodiments, at least two, three, four or more up to one hundred predetermined positions are associated with the ampoule, wherein the at least two predetermined positions in accordance with the invention are arranged asymmetrically on or on top of the ampoule.

Thus, in some embodiments, a first recognition element can be attached in a first of, for example, four available predetermined positions and a second recognition element can be attached at one of the then remaining three positions. By providing a multitude of predetermined positions for at least two recognition elements in accordance with the present invention, any ampoule can be clearly identified. For example, by attaching recognition elements at two selected positions of the predetermined positions relative to an ampoule filled with a first substance at a first concentration, and attaching two recognition elements at different selected positions of the predetermined positions relative to a different ampoule containing a different substance or the same substance with a different concentration, the two ampoules can be differentiated or distinguished.

In accordance with some embodiments of the present invention, the predetermined positions are arranged asymmetrically on an ampoule, e.g., they are not rotationally symmetrically located. In some embodiments, when, for example, four different positions are predetermined on a circle for attaching the recognition elements, the angular distance between any two positions is preferably not the same as the angular distance between any other two positions. The ampoule can thus be clearly identified. Additionally, security against errors in recognition is increased, since, due to the asymmetry, it is not possible to incorrectly determine the contents of an ampoule, coded by the arrangement of the recognition elements, by rotating the ampoule. Further, if an error occurs, e.g., because one of the recognition elements is faulty, has become separated from the ampoule, or there is a defect on the ampoule which acts as a recognition element, then such an error can be identified by ampoule recognition in accordance with the present invention and possibly even corrected.

As used herein, the term "asymmetrical" is to be understood in the sense of the invention such that by shifting and/or rotating an ampoule comprising, for example, two recognition elements in two selected particular positions of four possible predetermined positions, no arrangement of the at least two recognition elements on the ampoule can be obtained which corresponds to an arrangement of the at least two recognition elements on the ampoule for any other two of the four possible predetermined positions.

If the predetermined possible positions for recognition elements to be attached are arranged asymmetrically, e.g., they are not rotationally symmetrically located, then it is possible to prevent an incorrect signal being read due to the ampoule being incorrectly turned in or otherwise coupled to an injection device.

Advantageously, more positions are predetermined than recognition elements are used, wherein the same number—e.g., two—of recognition elements is always used at respectively different positions or a combination of positions to characterize an ampoule or a set of different ampoules.

In some preferred embodiments, the at least two predetermined positions or recognition elements are provided at one end of the ampoule, for example on the front side of the ampoule via which the ampoule is slid into an injection or infusion apparatus.

In some preferred embodiments, the predetermined positions or recognition elements are arranged substantially along a circle, wherein the circle is concentric with respect to a center axis of symmetry of the ampoule.

Advantageously, at least three predetermined positions are predetermined on an ampoule, at which the at least two recognition elements can be provided. However, any number of positions may be predetermined, e.g., four, five, fifty or more, for attaching at least two recognition elements.

It is also possible to provide more than two recognition elements, e.g., three, fifty or more, on an ampoule to be able to identify a multitude of different types of ampoules or ampoule fillings and to achieve as high a security or tolerance against errors as possible.

In some preferred embodiments, at least one of the at least two recognition elements is always fixedly arranged at a particular predetermined position, i.e., a predetermined position is always occupied by a recognition element which can serve as a reference recognition element. The arrangement of the at least one other recognition element relative to this reference recognition element can then be used to clearly identify an ampoule and/or its contents.

In addition to the arrangement described above, i.e., at least two recognition elements, each at one of at least two, or preferably three or four predetermined positions, at least two, or preferably three or four other reference recognition elements can also be provided, arranged for example on a circle, preferably with roughly the same angular distance between them. This circle is advantageously concentric with respect to a circle in which the predetermined positions described above for the at least two recognition elements lie. The reference recognition elements can be arranged inside or outside said circle of the recognition elements described above. Such an embodiment of the present invention enables a rotational movement of the ampoule, for example when the ampoule is screwed into an injection or infusion apparatus, to be recognized by detecting the reference recognition elements, preferably arranged at equal angular distances along a circle, and to detect—on the basis of this recognized rotational movement—in which of the predetermined positions the at least two recognition elements are arranged in or on the ampoule. Thus, for example, when screwing an ampoule into an injection apparatus by hand, the arrangement of the at least two recognition elements can be detected, despite a non-uniform screw-in movement. If, for example, four reference recognition elements are arranged at an angular distance of 90° and thus generate a signal every quarter turn, then it is possible to recognize whether the recognition elements are at two opposing predetermined positions or at two predetermined positions spaced at a acute angle.

In some embodiments, the recognition element(s) advantageously involves one or more of an electrical, magnetic, inductive, capacitive and/or mechanical principle. A magnet, such as a hard magnetic material or a permanent magnet, a soft magnetic or magnetizable material or a magnetic plastic or a plastic containing magnetic materials, can be used in accordance with the present invention as a recognition element. Additionally or alternatively, the recognition element can be formed as a conductive structure, an optical structure, a surface structure, an oscillating circuit, a chip, etc., and it may be adapted to have any suitable characteristic(s). In general, the recognition element should to be formed such that the presence or absence of a recognition element at a particular location can be detected. Recognition elements which generate electrical and/or magnetic fields of different strengths or polarities can be used, so as to be able to clearly detect a particular individual recognition element or a particular group of recognition elements by the orientation, polarity and/or strength of a field, and so be able to differentiate certain recognition elements from others.

In some preferred embodiments, the property of a recognition element can be altered, i.e., a magnetizable material reversed in polarity in the magnetizing direction in order to enable the recognition elements of an ampoule to be suitably programmed, such that information regarding the contents of the ampoule can be written into the recognition elements.

The administering device in accordance with the present invention, e.g., an infusion apparatus, to which an ampoule comprising at least two recognition elements can be coupled, e.g., inserted, screwed, etc., may be coupled to at least one ampoule and comprises at least two sensors—or three, four, five, fifty or more sensors—at predetermined positions, in order to be able to detect the presence or absence of a recognition element in the area of the sensor, e.g., near a sensor, in front of a sensor, using these sensors.

In accordance with an alternative aspect of the present invention, an administering device comprises at least one sensor which can be moved, for example, by means of a motor, along an ampoule inserted into the administering device, for example around or along the ampoule, in order to thereby detect the relative position of the at least two recognition elements associated with the ampoule.

If the ampoule is screwed into the administering device, the threads are advantageously aligned, i.e., the threads exhibit as tight a tolerance as possible, such that when the ampoule is fully screwed in it exhibits a particular predetermined positional relationship relative to the administering device. For example, when fully screwed in or attached, a particular point on the front side of an ampoule is at a predetermined position, and/or is advantageously only laterally distorted as little as possible with respect to the desired position.

Advantageously, a suitable end stopper, e.g., a protrusion, cam, etc., can be provided such that an ampoule—when slid or screwed in—comes to rest against the end stopper and cannot be turned further, so as to secure the position of the ampoule.

Advantageously, at least one positioning element is provided in the administering device, using which the at least one sensor or sensors can be suitably positioned, individually or together, for example on a circuit board. The sensors then preferably lie opposite the predetermined positions for the at least two recognition elements of the ampoule when the ampoule is inserted into the administering device. This can be on the front side of the ampoule and/or also on lateral areas of the ampoule.

In accordance with some embodiments of the invention, it is also possible to provide the sensors at a certain distance from the respective recognition elements when the ampoule is inserted, wherein suitable transfer elements can be provided, such as soft magnetic materials for deflecting magnetic fields, light conductors or electrical conductors for conducting physical properties or signals—specific to the respective recognition elements—to the respective sensors.

In some embodiments, the sensors can be formed as Hall sensors, light detectors, mechanical switches for detecting surface structures, electrical switches for determining an electrical resistance, a capacitance, an inductance or a resonance frequency, or other suitable detectors which are suitable for detecting the recognition elements used in each case.

In accordance with the present invention, a motor for inserting the ampoule into the administering device is provided, for example a motor for sliding or turning the ampoule in. If, the ampoule is turned by such a motor at a known and preferably constant speed when it is being turned in, then the positions of the at least two recognition elements arranged on the ampoule can be detected as soon as the ampoule is inserted into the administering device, for example by means of a single sensor fixedly arranged in the administering device, thus enabling the type and/or contents of the ampoule to be identified as soon as the ampoule is inserted into the administering device.

Advantageously, in some embodiments, at least one multiplexer is provided which is connected to at least two—and preferably to all—of the sensors used, in order to be able to reduce the number of signals to be transferred from the sensors to an evaluation logic. If, for example, four sensors are used, then the four signals received from the sensors can be transmitted via a multiplexer—for example, in a time multiplexing method—onto two or even just a single line, such that overall only a single signal line is required, which reduces wiring costs.

Advantageously, in some embodiments, a display may be attached to the administering device, using which the type of ampoule or ampoule contents detected by the sensors can be displayed in order to enable a user or observer to receive and/or verify the detection result.

In accordance with one aspect of the present invention, an ampoule embodiment, including one or more of those embodiments described herein, is combined with an embodiment of an administering device, including one or more of those embodiments described herein, to form an administering system.

BRIEF DESCRIPTION OF THE DRAWINGS

FIG. 2, including

FIG. 5, including

FIGS. 7A-C, depicts exemplary ways of connecting magnets to an ampoule;

DETAILED DESCRIPTION

Figure 1:
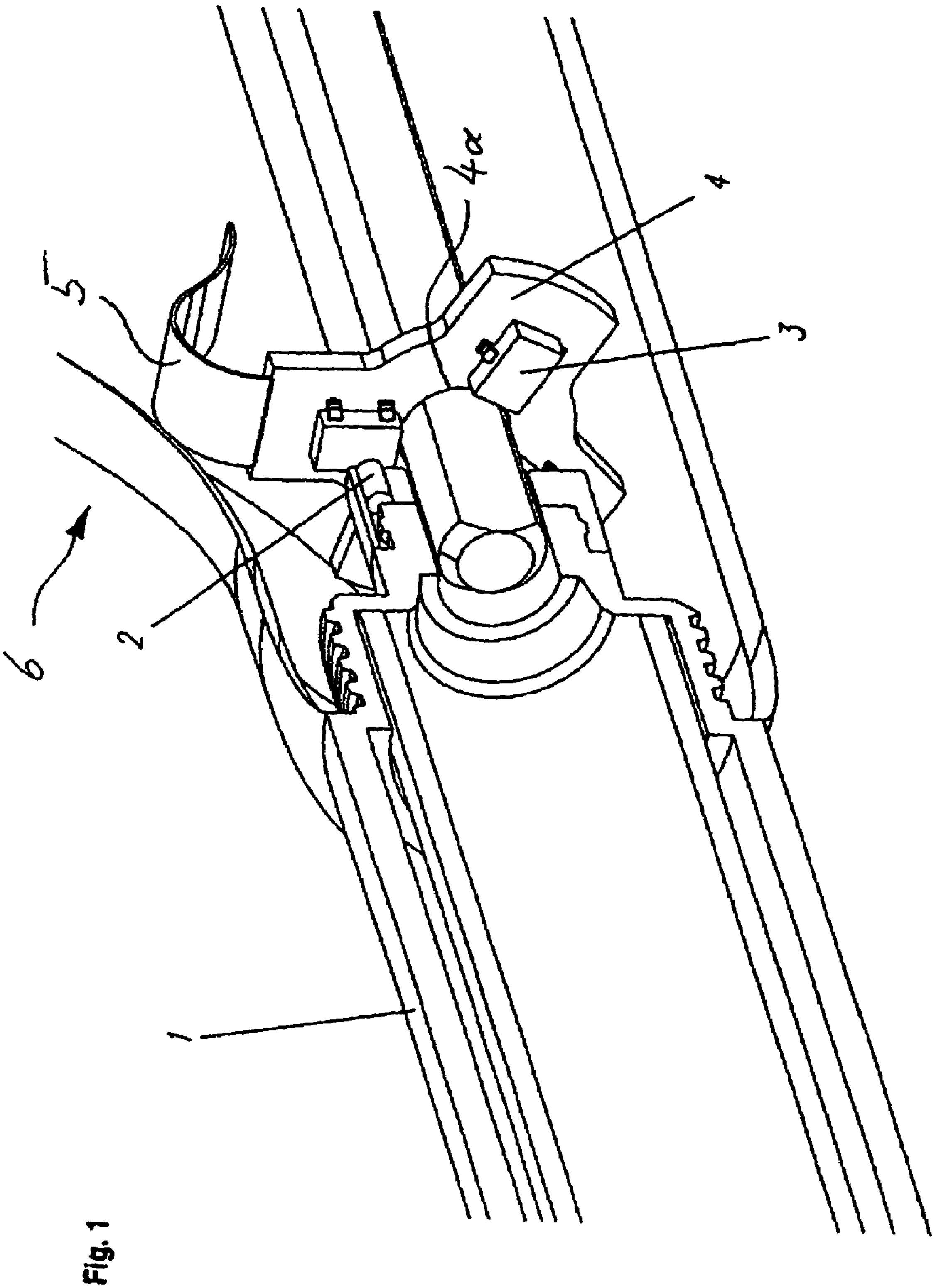
FIG. 1 is a perspective view of an ampoule in accordance with the present invention inserted into an injection pen.

FIG. 1 shows an ampoule 1 with rod-shaped magnets 2 arranged in it which serve as recognition elements. The ampoule 1 is screwed fully into the pen 6, such that each of the two magnets 2 arranged in the ampoule 1 lies opposite one of the four asymmetrically arranged sensors 3 which are arranged on a circuit board 4 and are fixedly connected to the pen 6. In order to correctly position the circuit board 4—with the sensors 3 arranged on it—on the pen 6, protrusions (not shown) are provided which engage with lateral cavities in the circuit board 4 and thus position the circuit board 4, secured against rotating, in the pen 6. In order to be able to transfer the signals from the sensors 3 to an evaluation logic, a flexible line connection 5 comprising a number of adjacent lines is connected to the circuit board 4. The pen 6 further comprises a battery (not shown), by which the sensors 3 and the evaluation logic (not shown) can be supplied with power. Above the mechanism holder, in which for example a threaded rod is guided which can pass through the circuit board 4 at a central opening 4*a*, a display device is arranged, on which the type of ampoule or ampoule contents detected by means of the magnets 2 and sensors 3 can be displayed. Any aspect of the present invention can be adapted so that the display can display any other information as well. A spring between the ampoule 1 and the circuit board 4 can ensure that the screwed-in ampoule has a stable fit.

Figure 2B:
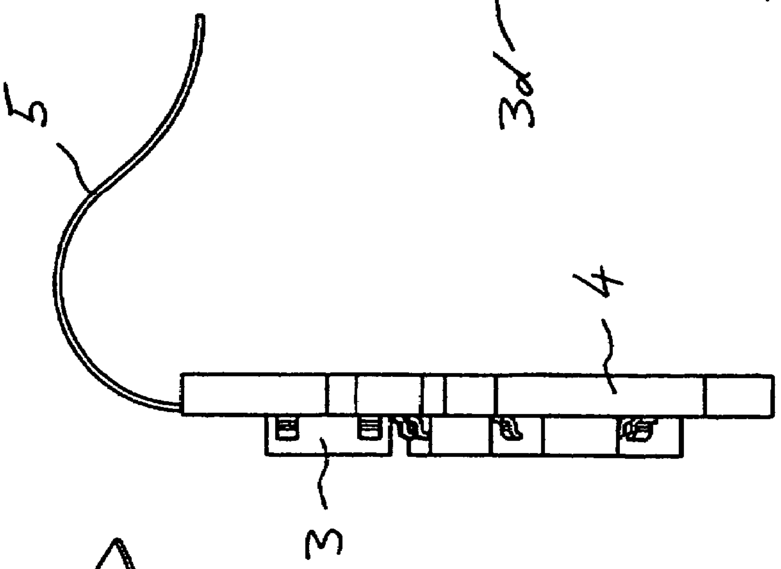
FIGS. 2A and 2B, depicts a circuit board with sensors attached to it.
Figure 2A:
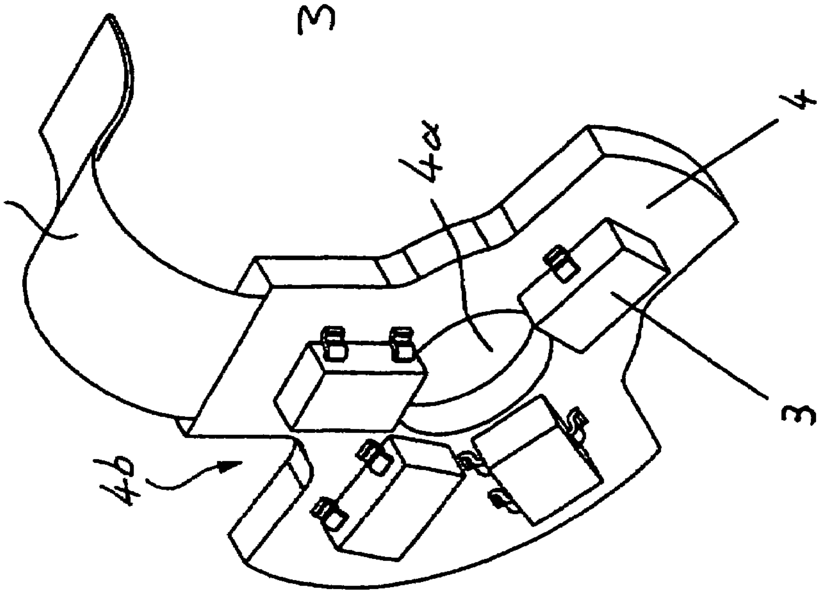

FIG. 2A shows a perspective view of the circuit board 4 shown in FIG. 1, with Hall sensors 3 arranged on it, wherein the circuit board 4 comprises lateral cavities 4*b* which in conjunction with the protrusions 10 shown in FIG. 1 serve to correctly position the circuit board 4 and therefore the Hall sensors 3 arranged on it. FIG. 2B shows a side view of the circuit board 4 shown in FIG. 2A.

Figure 3:
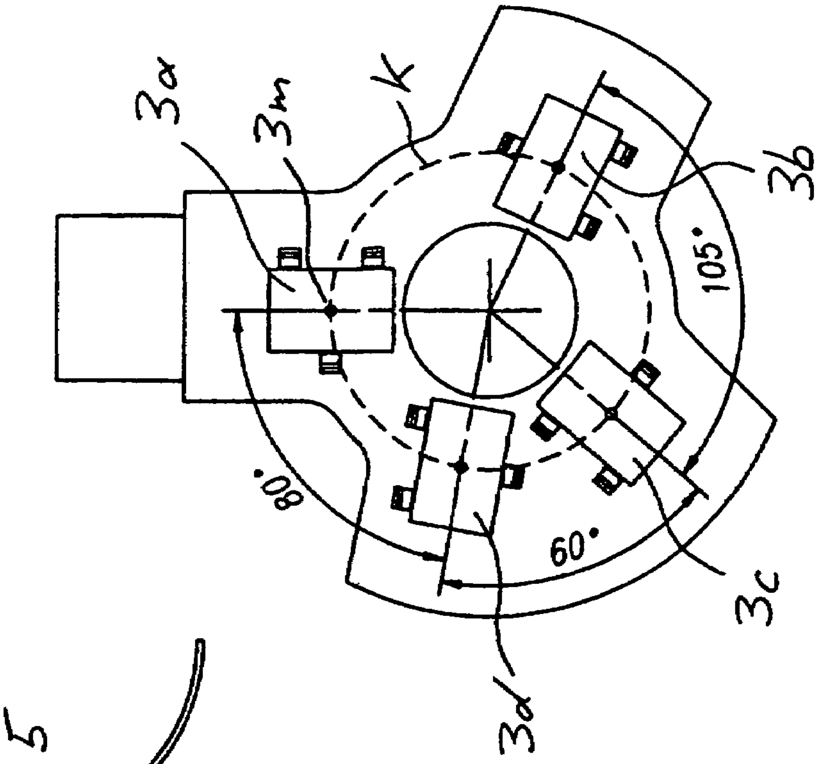
FIG. 3 is a schematic of the circuit board shown in FIG. 2A, and is provided to elucidate the asymmetrical arrangement of the sensors.

FIG. 3 shows an exemplary embodiment of the arrangement in accordance with the invention of four Hall sensors 3 on a circuit board 4. The center points 3*m* of the Hall sensors 3 are arranged along a circle K which is concentric with respect to the center axis of the abutting ampoule 1 when the latter is screwed into the pen 6. The angle between the Hall sensor 3*a* and the Hall sensor 3*b* is 115°, the angle between the Hall sensor 3*b* and the Hall sensor 3*c* is 105°, the angle between the Hall sensor 3*c* and the Hall sensor 3*d* is 60° and the angle between the Hall sensor 3*d* and the Hall sensor 3*a* is 80°. Consequently, the four Hall sensors 3*a* to 3*d* are arranged asymmetrically and are not rotationally symmetrical, and it is possible to recognize ampoules, secure against errors, when positions for accommodating the magnets 2 serving as recognition elements, corresponding to the positions of the Hall sensors, are provided in the ampoules. If, for example, the position on the ampoule corresponding to the position of the Hall sensor 3*a* is always occupied by a magnet 2, then three different types of ampoule can be clearly identified, if a first type of ampoule comprises a magnet only at the position corresponding to the Hall sensor 3*b*, a second type of ampoule comprises a magnet 2 at the position corresponding to the Hall sensor 3*c*, and a third type of ampoule comprises a magnet 2 at the position corresponding to the Hall sensor 3*d*.

If, for example, a magnet is damaged or lost, then at most one of the Hall sensors 3*a* to 3*d* emits a signal, such that it may be ascertained from this that there is a fault. If an ampoule is screwed in such that a reference magnet does not lie opposite the Hall sensor 3*a* as desired, then due to the asymmetrical arrangement of the sensors 3*a* to 3*d* shown, it is not possible to arrive at a configuration in which two magnets 2 arranged at predetermined positions of the ampoule 1 each oppose a Hall sensor 3. At most, only one of the magnets 2 attached at the predetermined positions in the ampoule 1 will be opposing one of the sensors 3*a* to 3*d*.

Figure 4:
FIG. 4 depicts an advantageous embodiment of the arrangement of recognition elements and sensors in accordance with the present invention.
Figure 5A:
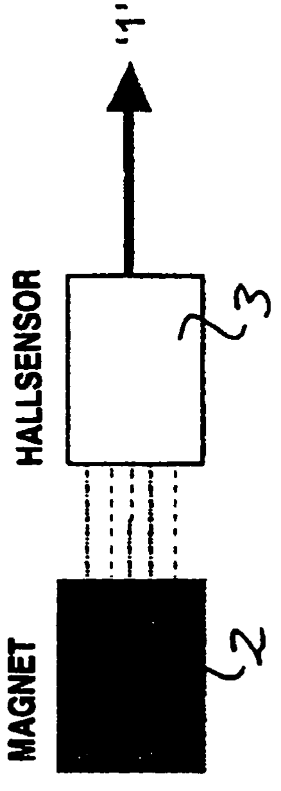
FIGS. 5A and 5B, is a schematic elucidation of the functional principle of magnetic detection.
Figure 5B:
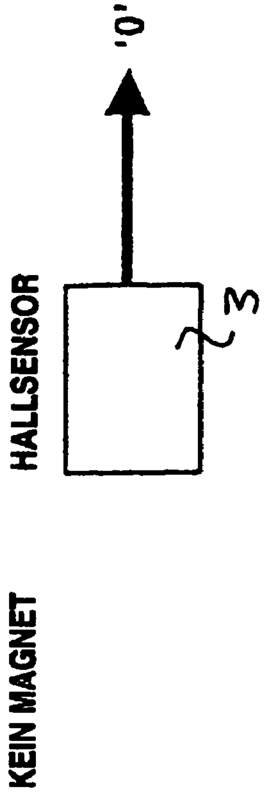

It is thus possible to detect—secure against errors —a type of ampoule and/or the contents of a particular ampoule, if the recognition elements 2 and sensors 3 are arranged asymmetrically in accordance with the invention. In general, the signals from the four Hall sensors 3*a* to 3*d* can be interpreted as a digital code word, wherein in order to generate such a code word, a sensor arrangement 3 lies opposite an arrangement of recognition elements 2 on the ampoule 1, as shown in FIG. 4. If an individual sensor 3, such as for example a Hall sensor, is opposed by a recognition element, i.e. for example a magnet 2, then this can be interpreted for example as a logical "1", as shown by way of example in FIG. 5A, while if a magnet is absent in front of the Hall sensor, a logical "0" is outputted, as shown by way of example in FIG. 5B. Other recognition elements 2 can also be used, instead of the magnets shown by way of example, with corresponding sensors 3.

If, for example, four sensors and two recognition elements are used, this consequently results in sixteen possible code words, as shown in the following table:

| Code word No. | abcd |
|---|---|
| 0 | 0000 |
| 1 | 0001 |
| 2 | 0010 |
| 3 | 0011 |
| 4 | 0100 |
| 5 | 0101 |
| 6 | 0110 |
| 7 | 0111 |
| 8 | 1000 |

-continued

| Code word No. | abcd |
|---|---|
| 9 | 1001 |
| 10 | 1010 |
| 11 | 1011 |
| 12 | 1100 |
| 13 | 1101 |
| 14 | 1110 |
| 15 | 1111 |

Only the code words 3, 5, 6, 9, 10 and 12 are valid code words, since all of the other code words comprise a logical "1" more or less than twice. If—as stated above—a recognition element is for example always arranged in the ampoule 1 such that is opposes a particular sensor—in the example in FIG. 3, for example, the sensor 3*a*—then the number of valid code words is reduced to three, being the code words with the numbers 9, 10 and 12, in which there is always a "1" at the position a. Such an asymmetrical code provides high security in recognition, with respect to errors occurring.

It is obvious that the invention can also be used with codes other than the codes set foprth above, which are presented for the purposes of description and elucidation, not to limit the invention.

Figure 6:
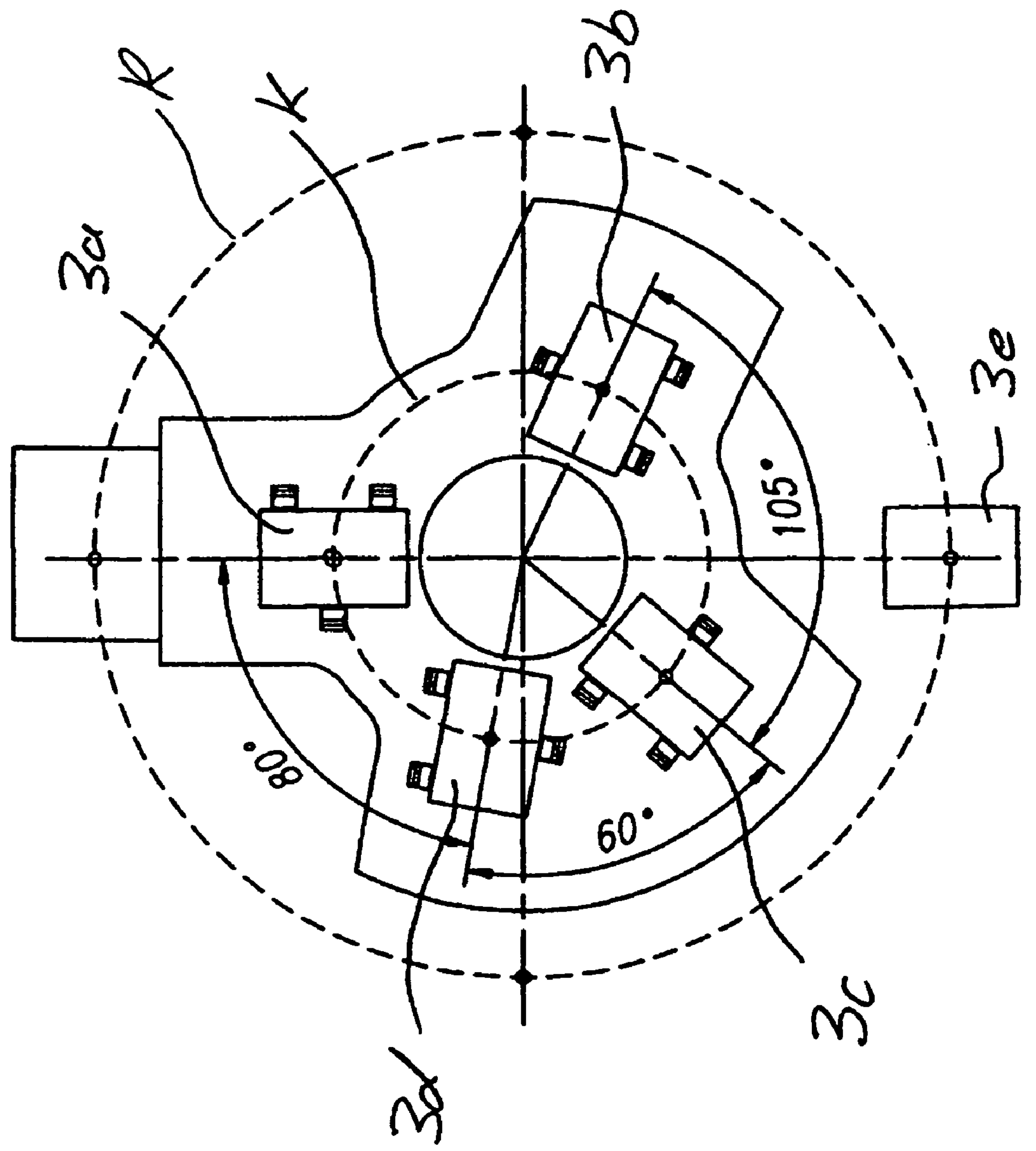
FIG. 6 depicts an embodiment of the present invention comprising reference recognition elements.

FIG. 6 shows a preferred embodiment of an arrangement of sensors 3 in accordance with the invention. In addition to the sensors 3*a* to 3*d*, whose arrangement corresponds to the arrangement described in FIG. 3, another Hall sensor 3*e* is provided in the exemplary embodiment shown, said sensor 3*e* lying outside the circle K on which the center points of the sensors 3*a* to 3*d* lie. If, for example, a number of recognition elements are arranged in an ampoule 1 to be screwed into an administering device, such that they are situated roughly on a circle R on which the center point of the other Hall sensor 3*e* is arranged, then when the ampoule is for example screwed into the pen 6, a rotational movement of the ampoule 1 can be recognized, for example by means of four magnets 2 arranged at an angular distance of 90° on the circle R, and in conjunction with the arrangement of magnets 2 in the ampoule 1 as described above, together with the arrangement of Hall sensors 3*a* to 3*d* shown by way of example, the position of the magnets 2 attached in positions corresponding to the Hall sensors 3*a* to 3*d* can be recognized even as the ampoule 1 is screwed in.

Figure 7:
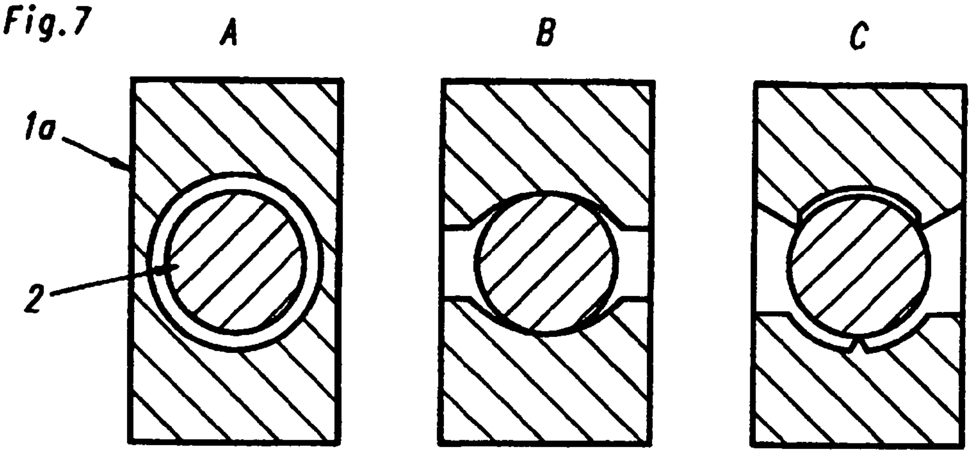
FIG. 7, including
Figure 8:
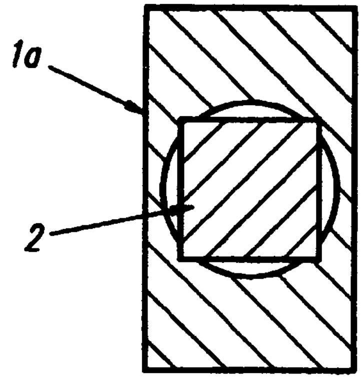
FIG. 8 depicts another exemplary way of connecting magnets to an ampoule.
Figure 9:
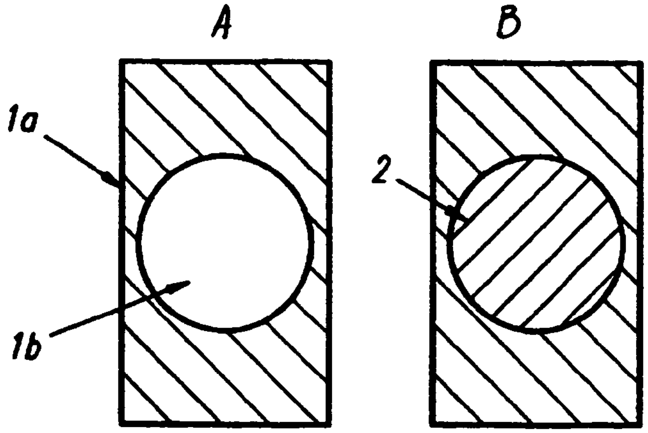
FIG. 9, including FIGS. 9A and B, depicts another exemplary way of providing an ampoule with magnets.

FIGS. 7, 8 and 9 show, by way of example, possible arrangements of magnets or other recognition elements in the ampoule 1, in particular in the front area of the circumference of the ampoule 1. Other embodiments of the recognition elements described above can also be correspondingly attached instead of the magnets 2.

FIG. 7, including FIGS. 7A-C, shows three exemplary embodiments for attaching a recognition element 2, e.g. a magnet 2 in the wall 1*a* of an ampoule 1, wherein the magnet 2 is formed cylindrical and is shown as a circular cross-section. In the embodiment shown in FIG. 7A, magnets 2 can be inserted in a cylindrical hollow space which exhibits a certain tolerance in their dimensions, wherein the magnets 2 can be either freely mounted in the corresponding hollow spaces or fixed using a suitable adhesive. FIGS. 7B and 7C show a magnet being fastened by clamping it in the ampoule wall 1*a*. It is advantageous here if the ampoule wall 1*a* consists of an elastic material such as for example a suitable plastic.

FIG. 8 shows an alternative embodiment for fastening a magnet 2 in an ampoule wall 1*a*, wherein the magnet 2 is formed parallelepipedal and can be deformed. If such a parallelepipedal magnet 2 is deformed at its edges and inserted into a cylindrical hollow space of the ampoule wall 1*a*, then the magnet 2 can be supported laterally in the ampoule wall 1*a* by its edges and thus be held fixedly in the ampoule wall 1*a*.

FIG. 9, including FIGS. 9A and B, shows another embodiment for forming a magnet 2 in an ampoule wall 1*a*, wherein a plastic emulsion comprising magnetic or magnetizable materials is inserted into a cylindrical hollow space 1*b* of the ampoule wall 1*a*.

For purposes of the present invention, recognition elements, sensors and other components, e.g., the multiplexer, microprocessor, display, etc., may be selected from any such devices with suitable characteristics and may be suitably arranged to accomplish the purpose of the invention, i.e., ampoule recognition. For example, the recognition elements may be associated with or carried by an administering device, the sensor or sensors then being associated with or carried by the ampoule. Further, the sensor or sensors may be embodied in a "stand alone" component or device, wherein the reading component or device would "read," i.e., recognize and/or identify, a recognition element or elements associated with an ampoule. Such an embodiment would be advantageous in, for example, ampoule manufacturing, filling, packaging or sorting.

In the foregoing description, embodiments of the present invention, including preferred embodiments, have been presented for the purpose of illustration and description. They are not intended to be exhaustive or to limit the invention to the precise forms disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An ampoule for an injection or infusion apparatus, said ampoule comprising:

a threaded surface parallel to a central longitudinal axis extending between a dispensing end and a distal end of said ampoule, said threaded surface providing a predetermined orientation of said ampoule when said threaded surface is engaged with an administering device, said distal end comprising a surface perpendicular to the axis;

at least four available predetermined recognition element positions positioned along a radius extending radially on the perpendicular surface about the longitudinal axis;

at least two recognition elements each positioned in one of the at least four predetermined recognition element positions;

wherein each of the predetermined recognition element positions is positioned asymetrically along the radius such that the circumferential distance between any two positions is different than the circumferential distance between any other two positions, wherein the number of available predetermined recognition element positions is greater than the number of recognition elements, and wherein the recognition elements are positioned in the predetermined element recognition positions such that detection of the positions of the recognition elements enables recognition of the ampoule.

2. The ampoule as set forth in claim 1, further comprising at least one reference recognition element on said ampoule, wherein the reference recognition element enables detection of the predetermined positions of the recognition elements while the ampoule is rotated.

3. The ampoule as set forth in claim 1, wherein a plurality of reference recognition elements are positioned along a second radius extending circumferentially on the perpendicular surface about the longitudinal axis, the first and second radii having different lengths.

4. The ampoule as set forth in claim 3, wherein said plurality of reference recognition elements are arranged to be circumferentially equidistant from one other along the second radius.

5. The ampoule as set forth in claim 1, wherein the at least two recognition elements are fabricated to enable detection of their positions using electrical, magnetic, inductive, capacitive or mechanical principles.

6. The ampoule as set forth in claim 5, wherein the at least two recognition elements are magnets, conductive structures, optical structures or surface structures.

7. The ampoule as set forth in claim 1, wherein the recognition elements may be written on said surface of said ampoule.

8. An ampoule for an injection or infusion apparatus, said ampoule comprising a threaded surface parallel to a central longitudinal axis extending between a dispensing end and a distal end of said ampoule, said threaded surface providing a predetermined orientation of said ampoule when said threaded surface is engaged with an administering device, said distal end comprising a surface perpendicular to the axis, wherein said surface comprises a set of at least four available predetermined recognition element positions positioned along a radius extending radially on the perpendicular surface about the longitudinal axis of said ampoule, wherein at least two recognition elements are each positioned in one of the at least four predetermined recognition element positions, wherein each of the predetermined recognition element positions is positioned asymetrically along the radius such that the circumferential distance between any two positions is different than the circumferential distance between any other two positions, wherein the number of available predetermined recognition element positions is greater than the number of recognition elements, and wherein the at least two recognition elements are positioned in the predetermined element recognition positions such that detection of the positions of the at least two recognition elements enables recognition of the ampoule.

9. An ampoule for an injection or infusion apparatus, said ampoule comprising:

a threaded surface parallel to a central longitudinal axis extending between a dispensing end and a distal end of said ampoule, said threaded surface providing a predetermined orientation of said ampoule when said threaded surface is engaged with an administering device, said distal end comprising a surface perpendicular to the axis;

at least four available predetermined recognition element positions positioned along a first radius extending radially on the perpendicular surface about the longitudinal axis;

at least two recognition elements each positioned in one of the at least four predetermined recognition element positions;

wherein each of the predetermined recognition element positions is positioned asymetrically along the first radius such that the circumferential distance between any two positions is different than the circumferential distance between any other two positions, wherein the number of available predetermined recognition element positions is greater than the number of recognition elements, and wherein the recognition elements are positioned in the predetermined element recognition positions such that detection of the positions of the recognition elements enables recognition of the ampoule; and a reference recognition element positioned along a second radius extending radially on the perpendicular surface about the longitudinal axis, the first and second radii having different lengths, wherein the reference recognition element enables detection of the positions of the recognition elements while the ampoule is rotated.

10. The ampoule as set forth in claim 9, further comprising a second reference recognition element positioned along the second radius, wherein each of the first and second reference recognition elements is provided at a circumferential distance from the other reference recognition element, the circumferential distance between the reference recognition elements being substantially the same circumferential distance.

* * * * *